United States Patent [19]

McCreary et al.

[11] 4,266,002

[45] May 5, 1981

[54] SUBSTITUTED 1-PHENYL-3-PYRAZOLIDINONE ELECTRON TRANSFER AGENTS

[75] Inventors: Michael D. McCreary; William C. Farley, both of Rochester; Wayne F. Erickson, Webster, all of N.Y.

[73] Assignee: Eastman Kodak Company, Rochester, N.Y.

[21] Appl. No.: 80,754

[22] Filed: Oct. 1, 1979

Related U.S. Application Data

[62] Division of Ser. No. 948,063, Oct. 2, 1978.

[51] Int. Cl.$^3$ .................... G03C 1/40; G03C 7/26
[52] U.S. Cl. .................... 430/218; 430/959; 548/379; 548/363
[58] Field of Search ............ 430/218, 959; 548/379, 548/363

[56] References Cited

U.S. PATENT DOCUMENTS

| | | | |
|---|---|---|---|
| 2,704,762 | 3/1955 | Kendall et al. | 430/483 |
| 2,743,279 | 4/1956 | Reynolds et al. | 260/465 |
| 2,772,282 | 11/1956 | Allen et al. | 430/469 |
| 2,983,606 | 5/1961 | Rogers | 430/218 |
| 3,039,869 | 6/1962 | Rogers et al. | 430/218 |
| 3,453,109 | 7/1969 | Lee | 430/464 |
| 3,740,221 | 6/1973 | Willems et al. | 430/234 |
| 3,980,479 | 9/1976 | Fields | 430/218 |
| 4,076,529 | 2/1978 | Fleckenstein et al. | 430/223 |
| 4,155,763 | 5/1979 | Hasebe et al. | 430/469 |

FOREIGN PATENT DOCUMENTS 1093281  11/1967  United Kingdom ............ 430/483

OTHER PUBLICATIONS

Research Disclosure, article 15162, Nov. 1976, p. 79.

*Primary Examiner*—Won H. Louie, Jr.
*Attorney, Agent, or Firm*—Harold E. Cole

[57] ABSTRACT

Photographic elements, film units, processes and alkaline processing compositions are described wherein certain substituted 1-phenyl-3-pyrazolidinones are employed as electron transfer agents in color image transfer materials. The silver halide electron transfer agents or precursors thereof have the following formula:

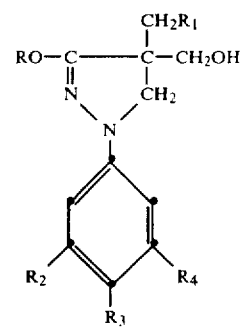

wherein:

R is hydrogen or a hydrolyzable moiety;
$R_1$ is hydrogen or a hydroxy group;
$R_2$, $R_3$ and $R_4$ each represent hydrogen, hydroxy, an alkyl group of 1 to 3 carbon atoms, an alkoxy group of 1 to 3 carbon atoms, a phenyl group, $-NHSO_2R_5$, $-O(CH_2)_nOR_6$, $-(CH_2)_nOR_6$, $-O(CH_2)_nC_6H_5$, $-(CH_2)_nR_7$, or $-O(CH_2)_nR_7$;
$R_5$ is hydrogen or an alkyl group of 1 to 3 carbon atoms;
$R_6$ is hydrogen or a methyl group;
$R_7$ is $NHSO_2R_5$ or $SO_2NHR_5$; and
n is a positive integer of 1 to 2;

with the proviso that at least one of $R_2$, $R_3$ and $R_4$ must be one of the groups other than hydrogen.

3 Claims, No Drawings

SUBSTITUTED 1-PHENYL-3-PYRAZOLIDINONE ELECTRON TRANSFER AGENTS

This is a division of application Ser. No. 948,063, filed Oct. 2, 1978.

This invention relates to photography, and more particularly to color diffusion transfer photography wherein certain substituted 1-phenyl-3-pyrazolidinones are used as electron transfer agents.

U.S. Pat. No. 4,076,529 of Fleckenstein et al, issued Feb. 28, 1978, describes various color image transfer elements which employ nondiffusible, redox-dye-releasing compounds which are alkali-cleavable upon oxidation to release a diffusible color-providing moiety. An electron transfer agent (ETA) is oxidized as a function of development. The $ETA_{ox}$ then cross-oxidizes the dye-releasing compound. The ETA compounds described therein include various pyrazolidinones, such as 1-phenyl-3-pyrazolidinone, 1-phenyl-4,4-dimethyl-3-pyrazolidinone and 4-hydroxymethyl-4-methyl-1-phenyl-3-pyrazolidinone. U.S. Pat. No. 3,740,221 and *Research Disclosure* article 15162, November, 1976, page 79, also disclose various 3-pyrazolidinones. Included therein is a compound having a methyl substituent on the phenyl ring, i.e., 4,4-dimethyl-1-tolyl-3-pyrazolidinone. While these compounds have been effective for their intended purposes, compounds which have a faster development rate which will give a faster access time for viewing the finished print are desired. The novel compounds employed in accordance with our invention achieve such a faster access time and, in addition, provide a lessening of crystal growth and bubbles in the processed print. Our substituted pyrazolidinone compounds can also be employed in a significantly lower concentration than the corresponding "unsubstituted" pyrazolidinone compounds to provide the sameamount of development.

The substituted 1-phenyl-3-pyrazolidinone compounds of our invention which are silver halide electron transfer agents or precursors thereof have the following formula:

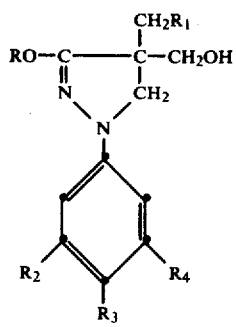

wherein:

R is hydrogen or a hydrolyzable moiety;
$R_1$ is hydrogen or a hydroxy group;
$R_2$, $R_3$ and $R_4$ each represent hydrogen, hydroxy, an alkyl group of 1 to 3 carbon atoms, such as methyl, ethyl and propyl, an alkoxy group of 1 to 3 carbon atoms, such as ethoxy, a phenyl group, $-NHSO_2R_5$, $-O(CH_2)_nOR_6$, $-(CH_2)_nOR_6$, $-O(CH_2)_nC_6H_5$, $-(CH_2)_nR_7$ or $-O(CH_2)_nR_7$;
$R_5$ is hydrogen or an alkyl group of 1 to 3 carbon atoms;
$R_6$ is hydrogen or a methyl group;
$R_7$ is $NHSO_2R_5$ or $SO_2NHR_5$; and
n is a positive integer of 1 to 2;
with the proviso that at least one of $R_2$, $R_3$ and $R_4$ must be one of the groups other than hydrogen.

R in the above formula can be hydrogen or any hydroylzable moiety well known to those skilled in the art, such as acetyl, mono-, di- or trichloroacetyl radicals, perfluoroacyl, pyruvyl, alkoxyacyl, nitrobenzoyl, cyanobenzoyl, sulfonyl, sulfinyl, etc.

When R in the above formula is hydrogen, the compound formula may be written in the enol form as:

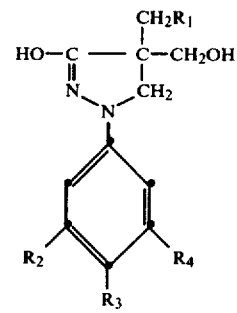

or in the keto form as:

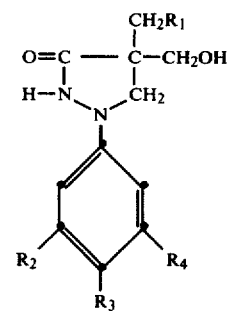

As used herein, the enol form is meant to include the keto form and vice versa.

When R in the above formula is a hydrolyzable moiety, then the compound is an ETA precursor and can be incorporated into a photographic element, cover sheet, receiving element, etc. When used in this manner, the ETA precursor can be employed in any concentration effective for the intended purpose. Good results have been obtained when the ETA precursor is employed at a concentraton of from about 0.2 to 1.8 m-moles/$m^2$ of element, preferably 0.5 to 1.5 m-moles/$m^2$.

When the hydrolyzable moiety R has been hydrolyzed, then the resulting ETA has the formula above where R is hydrogen. This can occur during processing of a photographic element containing the ETA precursor with an alkaline processing composition. Of course, when the ETA is located in an alkaline processing composition initially, then R is hydrogen also. When employed in an alkaline processing composition, good results have been obtained when the ETA is present at a concentration of from about 0.1 to about 30 grams per liter, and preferably from about 2 to about 12 grams per liter.

In a preferred embodiment of our invention, $R_1$ is hydrogen, $R_2$ is hydrogen, $R_3$ is an alkyl group of 1 to 3 carbon atoms, and R₄ is hydrogen. In a highly preferred embodiment of our invention, R₃ is a methyl group.

Examples of compounds useful as an ETA or precursor thereof in accordance with our invention have the following definitions in the above formula:

| Compound No. | R | $R_1$ | $R_2$ | $R_3$ | $R_4$ |
|---|---|---|---|---|---|
| 1 | H | H | H | $CH_3$ | H |
| 2 | H | H | H | $CH_2CH_3$ | H |
| 3 | H | OH | H | $CH_3$ | H |
| 4 | H | OH | H | $CH_2CH_3$ | H |
| 5 | H | H | H | $CH_2CH_2CH_3$ | H |
| 6 | H | H | $CH_3$ | $CH_3$ | H |
| 7 | $C_6H_5CO$ | H | $CH_3$ | H | $CH_3$ |
| 8 | H | H | H | $OCH_3$ | H |
| 9 | H | H | H | $C_6H_5$ | H |
| 10 | H | H | H | $NHSO_2CH_3$ | H |
| 11 | H | H | $NHSO_2CH_3$ | H | H |
| 12 | $CH_3CO$ | H | H | $CH_3$ | H |
| 13 | $C_6H_5CO$ | H | H | $CH_2CH_3$ | H |
| 14 | H | H | $OCH_3$ | $OCH_3$ | H |
| 15 | H | H | H | $OCH_2CH_2OH$ | H |
| 16 | $CH_3CO$ | H | H | $CH_2OCH_3$ | H |
| 17 | H | H | H | $CH_2CH_2OH$ | H |
| 18 | H | H | H | OH | H |

A photographic element according to our invention comprises a support having thereon at least one photosensitive silver halide emulsion layer having associated therewith a dye image-providing material, and containing an ETA precursor according to the formula above where R is a hydrolyzable moiety.

A dye image-receiving element according to our invention comprises a support having thereon a dye image-receiving layer and containing an ETA precursor according to the formula above where R is a hydrolyzable moiety.

The dye image-providing material useful in our invention can be positive- or negative-working, and can be initially mobile or immobile in the photographic element during processing with an alkaline composition. Examples of initially mobile, positive-working dye image-providing materials useful in our invention are described in U.S. Pat. Nos. 2,983,606; 3,536,739; 3,705,184; 3,482,972; 2,756,142; 3,880,658 and 3,854,985. Examples of negative-working dye image-providing materials useful in our invention include conventional couplers which react with oxidized aromatic primary amino color developing agents to produce or release a dye, such as those described, for example, in U.S. Pat. No. 3,227,550 and Canadian Pat. No. 602,607. In a preferred embodiment of our invention, the dye image-providing material is a ballasted, redox-dye-releasing (RDR) compound. Such compounds are well known to those skilled in the art and are, generally speaking, compounds which will redox with oxidized developing agent or electron transfer agent to release a dye, such as by alkaline hydrolysis, or prevent the release of dye, such as by intramolecular nucleophilic displacement. Such nondifusible RDR's can be positive-working compounds, as described in U.S. Pat. No. 3,980,479, British Pat. No. 1,464,104 and U.S. Pat. application Ser. No. 775,025, filed Mar. 7, 1977. Such nondiffusible RDR's can also be negative-working compounds, as described in U.S. Pat. Nos. 3,728,113 of Becker et al; 3,725,062 of Anderson and Lum; 3,698,897 of Gompf and Lum; 3,628,952 of Puschel et al; 3,443,939 and 3,443,940 of Bloom et al; 4,053,312 of Fleckenstein; 4,076,529 of Fleckenstein et al; 4,055,428 of Koyama et al; German Pat. Nos. 2,505,248 and 2,729,820; *Research Disclosure* 15157, November, 1976; and *Research Disclosure* 15654, April, 1977. In a more preferred embodiment of our invention, the nondiffusible RDR's are ballasted p-sulfonamidonaphthol compounds, each of which has a color-providing moiety attached thereto through a sulfonamido group which is alkali-cleavable upon oxidation.

A process for producing a photographic image in color according to our invention comprises:

treating an imagewise-exposed photographic element comprising a support having thereon at least one photosensitive silver halide emulsion layer having associated therewith a dye image-providing material with an alkaline processing composition in the presence of a silver halide ETA to effect development of each exposed silver halide emulsion layer, whereby:

(a) an imagewise distribution of dye is formed as a function of the development of the silver halide emulsion layer; and (b) at least a portion of the imagewise distribution of the dye diffuses out of the element, such as to a dye image-receiving layer.

In the above process, the ETA may be located in the alkaline processing composition or may be located in the photographic element (or in a cover sheet or receiving element) in its "blocked" or precursor form.

It will be appreciated that, after processing the element, after transfer has taken place, an imagewise distribution of dye in addition to developed silver. A color image comprising residual nondiffusible compound may be obtained in this element if the residual silver and silver halide are removed in any conventional manner well known to those skilled in the photographic art, such as a bleach bath followed by a fix bath, a bleach-fix bath, etc. The imagewise distribution of dye may also diffuse out of this element into these baths, if desired, rather than to an imge-receiving element.

The photographic element in the above-described process can be treated with an alkaline processing composition to effect or initiate development in any manner. A preferred method for applying processing composition is by use or a rupturable container or pod which contains the composition. The processing composition employed in this invention can contain the ETA for development, although the composition could also be solely an alkaline solution where the ETA is incorporated in the photographic element, the image-receiving element or the cover sheet. In these instances, the alkaline solution serves to activate the incorporated ETA.

A photographic assemblage or film unit in accordance with this invention is adapted to be processed by an alkaline processing composition, and comprises:

(1) a photographic element comprising a support having thereon at least one photosensitive silver halide emulsion layer having associated therewith a dye image-providing material; and (2) a dye image-receiving layer, the assemblage containing the ETA or precursor thereof as described above. In this embodiment, the processing composition may be inserted into the film unit such as by interjecting processing solution with communicating members similar to hypodermic syringes which are attached either to a camera or camera cartridge. The processing composition may also be applied by means of a swab or by dipping in a bath, if so desired. In a preferred embodiment of the invention, the assemblage itself contains the alkaline processing composition and means containing same for discharge within the film unit, such as a rupturable container which is adapted to be positioned during processing of the film unit so that a compressive force applied to the container by pressure-applying members, such as would be found in a camera designed for in-camera processing, will effect a discharge of the container's contents within the film unit. As previously described, the ETA can be located in the assemblage in the processing composition. Alternatively, an ETA precursor can be located in the photographic element or in an image-receiving element, cover sheet or process sheet, as described below.

The dye image-receiving layer in the above-described assemblage or film unit can be located on a separate support adapted to be superposed on the photographic element after exposure thereof. Such image-receiving elements are generally disclosed, for example, in U.S. Pat. No. 3,362,819. When the means for discharging the processing composition is a rupturable container, it is usually positioned in relation to the photographic element and the image-receiving element so that a compressive force applied to the container by pressure-applying members, such as would be found in a typical camera used for in-camera processing, will effect a dishcarge of the container's contents between the image-receiving element and the outermost layer of the photographic element. After processing, the dye image-receiving element is separated from the photographic element.

The dye image-receiving layer in the above-described assemblage or film unit can also be located integral with the photographic element between the support and the lowermost photosensitive silver halide emulsion layer. One useful format for integral receiver-negative photographic elements is disclosed in Belgian Pat. No. 757,960. In such an embodiment, the support for the photographic element is transparent and is coated with an image-receiving layer, a substantially opaque light-reflective layer, e.g., TiO$_2$, and then the photosensitive layer or layers described above. After exposure of the photographic element, a rupturable container containing an alkaline processing composition and an opaque process sheet are brought into superposed position. Pressure-applying members in the camera rupture the container and spread processing composition over the photographic element as the film unit is withdrawn from the camera. The processing composition develops each exposed silver halide emulsion layer, and dye images, formed as a function of development, diffuse to the image-receiving layer to provide a positive, right-reading image which is viewed through the transparent support on the opaque reflecting layer background. For other details concerning the format of this particular integral film unit, reference is made to the above-mentioned Belgian Pat. No. 757,960.

Another format for integral negative-receiver photographic elements in which the present invention can be employed is disclosed in Belgian Pat. No. 757,959. In this embodiment, the support for the photographic element is transparent and is coated with the image-receiving layer, a substantially opaque, light-reflective layer and the photosensitive layer or layers described above. A rupturable container, containing an alkaline processing composition and an opacifier, is positioned between the top layer and a transparent cover sheet which has thereon a neutralizing layer and a timing layer. The film unit is placed in a camera, exposed through the transparent cover sheet and then passed through a pair of pressure-applying members in the camera as it is being removed therefrom. The pressure-applying members rupture the container and spread processing composition and opacifier over the negative portion of the film unit to render it light-sensitive. The processing composition develops each silver halide layer and dye images, formed as a result of development, diffuse to the image-receiving layer to provide a positive, right-reading image which is viewed through the transparent support on the opaque reflecting layer backgound. For further details concerning the format of this particular integral film unit, reference is made to the above-mentioned Belgian Pat. No. 757,959.

Still other useful integral formats in which this invention can be employed are described in U.S. Pat. Nos. 3,415,644; 3,415,645; 3,415,646; 3,647,437; and 3,635,707. In most of these formats, a photosensitive silver halide emulsion is coated on an opaque support, and a dye image-receiving layer is located on a separate transparent support superposed over the layer outermost from the opaque support. In addition, this transparent support also preferably contains a neutralizing layer and a timing layer underneath the dye image-receiving layer.

Another embodiment of the invention uses the image-reversing technique disclosed in British Pat. No. 904,364, page 19, lines 1 through 41. In this process, the dye-releasing compounds are used in combination with physical development nuclei in a nuclei layer contiguous to the photosensitive silver halide negative emulsion layer. The film unit contains a silver halide solvent, preferably in a rupturable container with the alkaline processing composition.

The film unit or assembly of the present invention may be used to produce positive images in single-or multi-colors. In a three-color system, each silver halide emulsion layer of the film assembly will have associated therewith a dye image-providing material which possesses a predominant spectral absorption within the region of the visible spectrum to which said silver halide emulsion is sensitive, i.e., the blue-sensitive silver halide emulsion layer will have a yellow dye image-providing material associated therewith, the green-sensitive silver halide emulsion layer will have a magenta dye image-providing material associated therewith, and the red-sensitive silver halide emulsion layer will have a cyan dye image-providing material associated therewith. The dye image-providing material associated with each silver halide emulsion layer may be contained either in the silver halide emulsion layer itself or in a layer contiguous to the silver halide emulsion layer, i.e., the dye image-providing material may be coated in a separate layer underneath the silver halide emulsion layer with respect to the exposure direction.

The concentration of the dye image-providing material that is employed in the present invention may be varied over a wide range, depending upon the particular compound employed and the results desired. For example, the dye image-providing material may be coated in a layer at a concentration of 0.1 to 3 g/m$^2$. The dye image-providing material may be dispersed in a hydrophilic film-forming natural material or synthetic polymer, such as gelatin, polyvinyl alcohol, etc., which is adapted to be permeated by aqueous alkaline processing composition.

In using dye image-providing materials in the invention which produce diffusible dye images as a function of development, either conventional negative-working or direct-positive silver halide emulsions may be employed. If the silver halide emulsion employed is a direct-positive silver halide emulsion, such as an internal-image emulsion designed for use in the internal image reversal process, or a fogged, direct-positive emulsion such as a solarizing emulsion, which is developable in unexposed areas, a positive image can be obtained on the dye image-receiving layer by using ballasted, redox, dye-releasers. After exposure of the film unit, the alkaline processing composition permeates the various layers to initiate development of the exposed photosensitive silver halide emulsion layers. The ETA present in the film unit develops each of the silver halide emulsion layers in the unexposed areas (since the silver halide emulsions are direct-positive ones), thus causing the ETA to become oxidized imagewise corresponding to the unexposed areas of the direct-positive silver halide emulsion layers. The oxidized ETA then cross-oxidizes the dye-releasing compounds and the oxidized form of the compounds then undergoes a base-catalyzed reaction to release the dyes imagewise as a function of the imagewise exposure of each of the silver halide emulsion layers. At least a portion of the imagewise distributions of diffusible dyes diffuse to the image-receiving layer to form a positive image of the original subject. After being contacted by the alkaline processing composition, a pH-lowering layer in the film unit or image-receiving unit lowers the pH of the film unit or image receiver to stabilize the image.

Internal-image silver halide emulsions useful in this invention are described more fully in the November 1976 edition of *Research Disclosure*, pages 76 through 79, the disclosure of which is hereby incorporated by reference.

The various silver halide emulsion layers of a color film assembly employed in this invention can be disposed in the usual order, i.e., the blue-sensitive silver halide emulsion layer first with respect to the exposure side, followed by the green-sensitive and red-sensitive silver halide emulsion layers. If desired, a yellow dye layer or a yellow colloidal silver layer can be present between the blue-sensitive and green-sensitive silver halide emulsion layers for absorbing or filtering blue radiation that may be transmitted through the blue-sensitive layer. If desired, the selectively sensitized silver halide emulsion layers can be disposed in a different order, e.g., the blue-sensitive layer first with respect to the exposure side, followed by the red-sensitive and green-sensitive layers.

The rupturable container employed in certain embodiments of this invention can be of the type disclosed in U.S. Pat. Nos. 2,543,181; 2,643,886; 2,653,732; 2,723,051; 3,056,492; 3,056,491 and 3,152,515. In general, such containers comprise a rectangular sheet of fluid- and air-impervious material folded longitudinally upon itself to form two walls which are sealed to one another along their longitudinal and end margins to form a cavity in which processing solution is contained.

Generally speaking, except where noted otherwise, the silver halide emulsion layers employed in the invention comprise photosensitive silver halide dispersed in gelatin and are about 0.6 to 6 microns in thickness; the dye image-providing materials are dispersed in an aqueous alkaline solution-permeable polymeric binder, such as gelatin, as a separate layer about 0.2 to 7 microns in thickness; and the alkaline solution-permeable polymeric interlayers, e.g., gelatin, are about 0.2 to 5 microns in thickness. Of course, these thicknesses are approximate only and can be modified according to the product desired.

Any material can be employed as the image-receiving layer in this invention as long as the desired function of mordanting or other wise fixing the dye images is obtained. The particular material chosen will, of course, depend upon the dye to be mordanted. Suitable materials are disclosed on pages 80 through 82 of the November 1976 edition of *Research Disclosure*, the disclosure of which is hereby incorporated by reference.

Use of a pH-lowering material in the film units of this invention will usually increase the stability of the transferred image. Generally, the pH-lowering material will effect a reduction in the pH of the image layer from about 13 or 14 to at least 11 and preferably 5 to 8 within a short time after imbibition. Suitable materials and their functions are disclosed on pages 22 and 23 of the July 1974 edition of *Research Disclosure*, and pages 35 through 37 of the July 1975 edition of *Research Disclosure*, the disclosures of which are hereby incorporated by reference.

A timing or inert spacer layer can be employed in the practice of this invention over the pH-lowering layer which "times" or controls the pH reduction as a function of the rate at which the alkaline composition diffuses through the inert spacer layer. Examples of such timing layers and their functions are disclosed in the *Research Disclosure* articles mentioned in the paragraph above concerning pH-lowering layers.

The alkaline processing composition employed in this invention is the conventional aqueous solution of an alkaline material, e.g., alkali metal hydroxides or carbonates such as sodium hydroxide, sodium carbonate or an amine such as diethylamine, preferably processing a pH in excess of 11, and preferably containing an ETA as described previously. Suitable materials and addenda frequently added to such compositions are disclosed on pages 79 and 80 of the November 1976 edition of *Research Disclosure*, the disclosure of which is hereby incorporated by reference.

The alkaline solution-permeable, substantially opaque, light-reflective layer employed in certain embodiments of photographic film units used in this invention are described more fully in the November 1976 edition of *Research Disclosure*, page 82, the disclosure of which is hereby incorporated be reference.

The supports for the photographic elements used in this invention can be any material, as long as it does not deleteriously affect the photographic properties of the film unit and is dimensionally stable. Typical flexible sheet materials are described on page 85 of the November 1976 edition of *Research Disclosure*, the disclosure of which is hereby incorporated by reference.

While the invention has been described with reference to layers of silver halide emulsions and dye image-providing materials, dotwise coating, such as would be obtained using a gravure printing technique, could also be employed. In this technique, small dots of blue-, green- and red-sensitive emulsions have associated therewith, respectively, dots of yellow, magenta and cyan color-providing substances. After developement, the transferred dyes would tend to fuse together into a continuous tone.

The silver halide emulsions useful in this invention, both negative-working and direct-positive ones, are well known to those skilled in the art and are described in *Product Licensing Index*, Volume No. 92, December 1971, publication 9332, page 107, paragraph I, "Emulsion types"; they may be chemically and spectrally sensitized, as described on page 107, paragraph III, "Chemical sensitization", and pages 108 and 109, paragraph XV, "Spectral sensitization", of the above article; they can be protected against the production of fog and can be stabilized against loss of sensitivity during keeping by employing the materials described on page 107, paragraph V, "Antifoggants and stabilizers", of the above article; they can contain development modifiers, hardeners, and coating aids as described on pages 107 and 108, paragraph IV, "Development modifiers"; paragraph VII, "Hardeners"; and paragraph XII, "Coating aids", of the above article; they and other layers in the photographic elements used in this invention can contain plasticizers, vehicles and filter dyes described on page 108, paragraph XI, "Plasticizers and lubricants", and paragraph VIII, "Vehicles", and page 109, paragraph XVI, "Absorbing and filter dyes", of the above article; they and other layers in the photographic elements used in this invention may contain addenda which are incorporated by using the procedures described on page 109, paragraph XVII, "Methods of addition", of the above article; and they can be coated by using the various techniques described on page 109, paragraph XVIII, "Coating procedures", of the above article, the disclosures of which are hereby incorporated by reference.

The term "nondiffusing" used herein has the meaning commonly applied to the term in photography and denotes materials that for all practical purposes do not migrate or wander through organic colloid layers, such as gelatin, in the photographic elements of the invention in an alkaline medium and preferably when processed in a medium having a pH of 11 or greater. The same meaning is to be attached to the term "immobile". The term "diffusible" is applied to the materials of this invention has the converse meaning and denotes materials having the property of diffusing effectively through the colloid layers of the photographic elements in an alkaline medium. "Mobile" has the same meaning as "diffusible".

The term "associated therewith" as used herein is intended to mean that the materials can be in either the same or different layers so long as the materials are accessible to one another.

The following examples are provided to further illustrate the invention.

EXAMPLE 1

Preparation of Compound 1

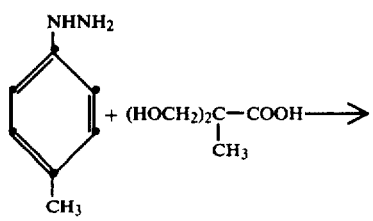

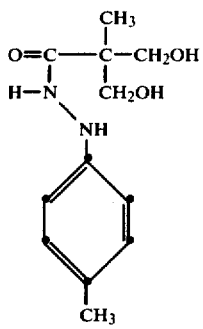

Sixty-five grams (0.49 m) of 2,2-bi(hyroxymethyl) propionic acid was added to a solution of p-tolylhydrazine (100 g, 0.44 m) and dicyclohexylcarbodiimide (100 g, 0.49 m) in 2,500 ml of tetrahydrofuran. The reaction mixture was stirred under a nitrogen atmosphere for 24 hours. The dicyclohexylurea was removed by filtration and the solution was concentrated under reduced pressure. The residue was recrystallized from 300 ml of isopropyl alcohol. There was obtained 71 g (68 percent) of 2,2-bishydroxymethyl propionic acid p-tolylhydrazide, m.p. 129 to 130° C.

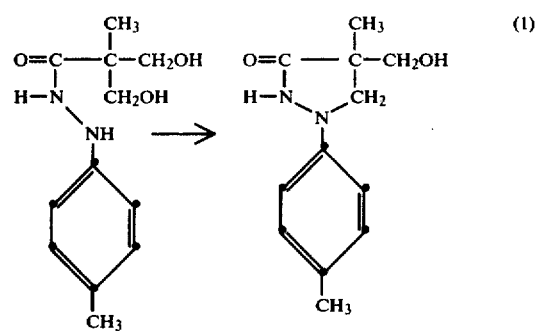

Seventy-one grams (0.30 m) of 2,2-bishydroxymethyl propionic acid p-tolylhydrazide, 3 g of p-toluene sulfonic acid and 500 ml of benzene were heated at reflux under a nitrogen atmosphere for 24 hours. The water formed was removed by azeotropic distillation. The reaction mixture was filtered hot and cooled to room temperature. The yellow solid which crystallized was collected and recrystallized from 150 ml of acetone. There was obtained 36 g (55 percent) of compound 1, 1-p-tolyl-4-hydroxymethyl-4-methyl-3-pyrazolidinone, m.p. 118° to 120° C.

EXAMPLE 2

Preparation of Compound 2

Example 1 was repeated, except that 4'-ethylphenylhydrazine was employed instead of p-tolylhydrazine. The intermediate 2,2-bis(hydroxymethyl) propionic acid p-ethylphenylhydrazide was recrystallized from isopropyl alcohol and had an m.p. of 120° to 122° C. Compound 2, 1-(4'-ethylphenyl)-4-hydroxymethyl-4-methyl-3-pyrazolidinone, was recrystallized from acetone and had an m.p. of 106° to 108° C.

EXAMPLE 3

Retained Image Format—Comparative Test

To evaluate Compound 1, shown above, and a closely-related control ETA Compound A with respect to their effectiveness as an ETA in a retained image format, the following photographic element was prepared by coating the following layers in the order recited on a cellulose acetate film support. Quantities are parenthetically given in g/m².

(1) green-sensitive, negative, 0.8 μ silver bromide emulsion (silver - 1.08, gelatin - 3.24);
(2) magenta RDR A (1.19) and 1,4-cyclohexylenedimethylene bis(2-ethylhexanoate) (0.594); and
(3) gelatin (0.864).

MAGENTA RDR A

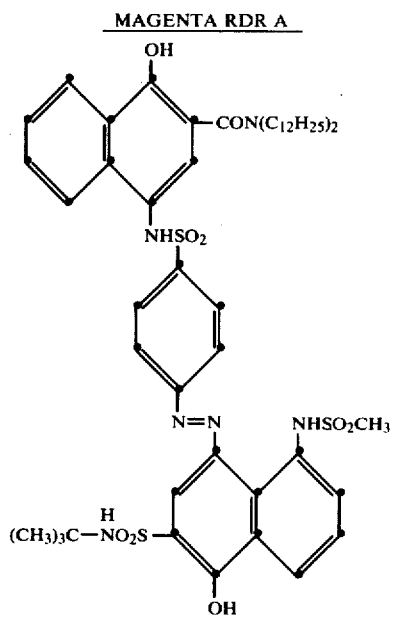

CONTROL ETA COMPOUND A

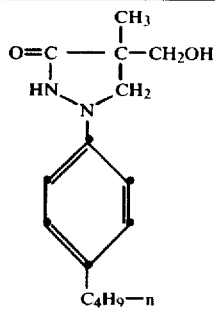

Samples of the above-prepared photosensitive element were exposed through a graduated-density test object. The exposed samples were then processed at 70° F. (21° C.) using a viscous processing composition, described below, between the exposed samples and a receiving element which constituted of a cellulose acetate film support coated with the mordant poly(divinylbenzene-co-styrene-co-N-benzyl-N,N-dimethyl-N-vinylbenzyl)ammonium chloride latex mordant (2.29 g/m²) and gelatin (2.29 g/m²).

| Processing Composition I | | |
|---|---|---|
| Potassium hydroxide | 30 | g |
| Potassium bromide | 0.75 | g |
| Sodium sulfite | 2.0 | g |
| Hydroxyethylcellulose | 25 | g |
| Control ETA Compound A | 2.5 | millimoles |
| Water to 1 liter | | |

Processing Composition II

Same as I, except that Compound 1 was employed, instead of Control ETA Compound A The receiving element was peeled apart at different time intervals and discarded, while the photographic element containing the retained image was washed, bleach-fixed in an ammonium ferric ethylenediaminetetraacetic acid/ammonium thiosulfate solution, washed, buffered to pH 10 in a sodium carbonate-sodium hydroxide solution, washed and dried.

Sensitometric results were then obtained and a plot of dye density versus time was generated. The time of dye clean-out (change from $D_{max}$ to $D_{min}$) for each ETA tested, measured at 0.2 below $D_{max}$, was as follows:

| ETA | Time of Clean-Out (seconds) |
|---|---|
| Control ETA Compound A | 13.5 |
| Compound 1 | 4.5 |

The above results indicate that Compound 1 of the invention gives a much faster rate of dye clean-out than the closely-related control compound.

EXAMPLE 4

Retained Image Format—Deep Tank Process—Comparative Test

To evaluate Compound 2 and closely-related prior art control ETA Compound B with respect to their effectiveness as an ETA in a retained image format for deep tank processing, the following photographic element was prepared by coating the following layers in the order recited on a cellulose acetate film support. Quantities are parenthetically given in g/m².

(1) anti-halation layer of silver (0.27) and gelatin (1.03);
(2) red-sensitive, negative, fine-grain silver bromide emulsion (silver - 0.65, gelatin - 1.40), cyan RDR B (0.78), and 1,4-cyclohexylenedimethylene bis(2-ethylhexanoate) (0.39);
(3) red-sensitive, negative, coarse-grain silver bromide emulsion (silver - 0.65, gelatin - 1.08), cyan RDR B (0.26) and 1,4-cyclohexylenedimethylene bis(2-ethylhexanoate) (0.131 ); and
(4) gelatin (1.03), ETA Scavenger, 2,5-di-sec-dodecylhydroquinone (0.43), and hardener bis(vinylsulfonylmethyl)ether (one percent).

CYAN RDR B

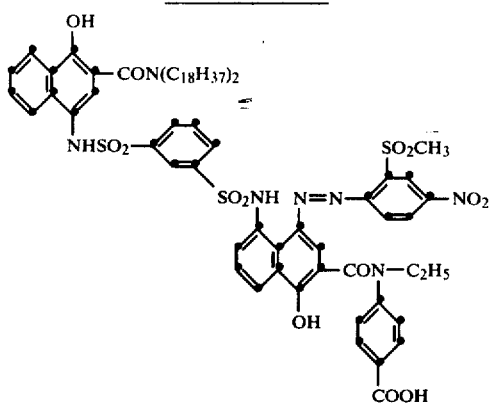

CONTROL ETA COMPOUND B

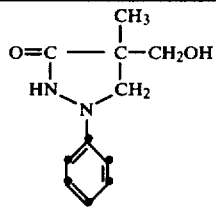

Samples of the above-prepared photosensitive element were exposed through a graduated-density test object. The exposed samples were then processed for 40 seconds in a processing composition, described below, washed, bleach-fixed in an ammonium ferric ethylenediaminetetraacetic acid/ammonium thiosulfate solution, washed in a pH 12.4 bath and dried.

| Processing Composition | | |
|---|---|---|
| $Na_3PO_4 \cdot 12H_2O$ | 38.8 | g |
| Potassium bromide | 2.5 | g |
| Sodium sulfite | 1.0 | g |
| 11-Aminoundecanoic acid | 2.0 | g |
| Hydroxylamine sulfate | 0.025 | g |
| Compound 2 or | 0.56 | g or |
| Control ETA Compound B | 0.5 | g |
| Water to 1 liter | | |

Sensitometric results were then obtained and a plot of relative threshold speed versus time of development was generated. The relative threshold speed, measured at 0.2 below $D_{max}$, for each ETA tested was as follows:

| ETA | Relative Threshold Speed (Log E) |
|---|---|
| Control ETA Compound B | 0.30 |
| Compound 2 | 0.65 |

The above results indicate that Compound 2 of the invention has a much higher relative threshold speed than Control ETA Compound B and thus is a more active ETA in a retained image format.

EXAMPLE 5

Preparation and Photographic Testing of Integral Imaging Receiving Element—Comparative Test To evaluate Compounds 1, 2 and closely-related prior art control ETA Compound B with respect to their effectiveness as an ETA in an integral imaging receiving element, the following photographic element was prepared by coating the following layers in the order recited on a transparent poly(ethylene terephthalate) film support. Quantities are parenthetically given in g/m², unless otherwise stated.

(1) image-receiving layer of a poly(divinylbenzene-co-styrene-co-N-benzyl-N,N-dimethyl-N-vinylbenzyl-)ammonium sulfate latex mordant (2.3) and gelatin (2.3);

(2) reflecting layer of titanium dioxide (16) and gelatin (2.6);

(3) opaque layer of carbon black (1.9) and gelatin (1.2);

(4) cyan dye-providing layer of gelatin (1.2), cyan RDR C (0.3), dispersed in 1,4-cyclohexylenedimethylene bis(2-ethylhexanoate) and gelatin (0.7);

(5) red-sensitive, direct-positive silver bromide emulsion (silver - 0.9, gelatin - 0.9), 1-[4-(2-formylhydrazino)phenyl]-3-methylthiourea (0.01), 2-(2-octadecyl-5-sulfohydroquinone potassium salt (0.2), and aceto-2-{p-[5-amino-2-(2,4-di-t-pentylphenoxy)-benzamido]phenyl}hydrazide (0.1);

(6) interlayer of gelatin (1.6) and 2,5-di-sec-dodecylhydroquinone (1.3);

(7) magenta dye-providing layer of magenta RDR D (0.3) dispersed in 1,4-cyclohexylenedimethylene-bis(2-ethylhexanoate) and gelatin (0.7);

(8) green-sensitive, direct-positive silver bromide emulsion (silver - 0.9, gelatin - 0.9), 1-[4-(2-formylhydrazino)phenyl]-3-methylthiourea (0.01), aceto-2-{[5-amino-2-(2,4-di-t-pentylphenoxy)benzamido]-phenyl}hydrazide (0.4), and 2-(2-octadecyl-5-sulfohydroquinone potassium salt (0.2);

(9) interlayer of gelatin (1.6) and 2,5-di-sec-dodecylhydroquinone (1.3);

(10) yellow dye-providing layer of yellow RDR E (0.4) dispersed in 1,4-cyclohexylenedimethylene-bis(2-ethyl-hexanoate) and gelatin (0.7);

(11) blue-sensitive, direct-positive silver bromide emulsion (silver - 0.9, gelatin - 0.9), 1-[4-(2-formylhydrazino)phenyl]-3-methylthiourea (0.005), aceto-2-{p-[5-amino-2-(2,4-di-t-pentylphenoxy)benzamido]-phenyl}hydrazide (0.2), and 2-(2-octadecyl-5-sulfohydroquinone potassium salt (0.2); and

(12) overcoat layer of gelatin (0.9).

CYAN RDR C

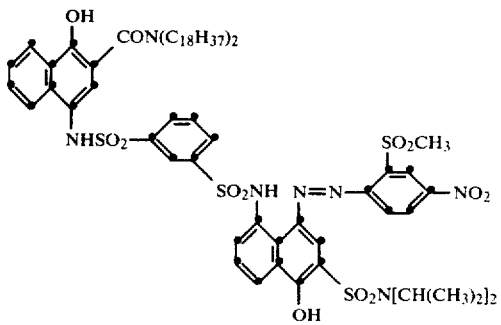

MAGENTA RDR D

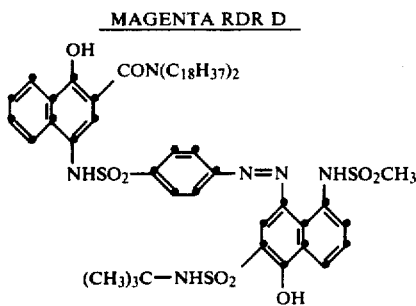

YELLOW RDR E

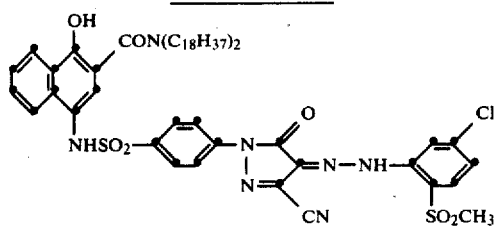

Samples of the above-prepared photosensitive elements where exposed through a multicolor graduated-density test object. The exposed samples were then processed under dark conditions at 72° F. (22° C.) by rupturing a pod containing the viscous processing compositions described below between the photosensitive element and a transparent cover sheet, as described below.

The processing compositions were as follows:

| Processing Composition A | | |
|---|---|---|
| Potassium hydroxide (45 percent aqueous solution) | 104 | g |
| Sodium sulfite | 1.0 | g |
| 5-Methylbenzotriazole | 4 | g |
| Control ETA Compound B | 12.0 | g |
| 1,4-Cyclohexanedimethanol | 1 | g |
| Sodium salt of naphthalene-formaldehyde condensate | 6.4 | g |
| Potassium fluoride . 2H$_2$O | 10.0 | g |
| Carboxymethylcellulose | 44.0 | g |
| Water to 1 liter | | |

Processing Composition B

Same as A, except that the ETA was Compound 1 at an equimolar concentration of 12.8 grams per liter

Processing Composition C

Same as A, except that the ETA was Compound 2 at an equimolar concentration of 13.6 grams per liter The cover sheet consisted of a transparent poly(ethylene terephthalate) film support having coated thereon:
(1) a polyacrylic acid layer (17.5 meq/0.093 m$^2$)
(2) a timing layer comprising a polymeric mixture as disclosed in an application by our coworker Abel, entitled "Barrier Layer Between Reactants in Photographic Products Comprising a Mixture of Vinylidene Chloride Terpolymer and Polymeric Carboxy-Ester-Lactone", U.S. Application Ser. No. 948,062, filed of even date herewith.

Initial access times, which are defined as the time that the transferred dye image is first visible to the eye, were determined for each of the elements as follows:

| Processing Composition | ETA | Initial Access Time (seconds) |
|---|---|---|
| A | Control ETA Compound B | 52 |
| B | Compound 1 | 31 |
| C | Compound 2 | 26 |

The above results indicate that use of Compound 1 of the invention gave a 40 percent improvement in initial access time over that obtained using Control ETA Compound B. In a similar manner, Compound 2 of the invention gave a 50 percent improvement.

EXAMPLE 6

Photographic Testing of Integral Imaging Receiving Element—Comparative Test

Compound 1 and several closely-related prior art control compounds, including two which are disclosed in *Research Disclosure*, Item 15162, November, 1976, page 79, were evaluated for their effectiveness as an ETA in an integral imaging receiving element. Samples of the integral imaging receiving element of Example 5 were exposed and processed in the same manner as in Example 5 using the following processing compositions:

| Processing Composition D | | |
|---|---|---|
| Potassium hydroxide | 47 | g |
| Sodium sulfite | 1.0 | g |
| 5-Methylbenzotriazole | 5 | g |
| Compound 1 | 12.8 | g |
| Sodium salt of naphthalene-formaldehyde condensate | 6.4 | g |
| Potassium fluoride | 6 | g |
| Carboxymethyl cellulose | 43.6 | g |
| Water to 1 liter | | |

Processing Composition E

Same as D, except that the ETA was Control ETA Compound B at an equimolar concentration of 12 g per liter.

Processing Composition F

Same as D, except that the ETA was Control ETA Compound C at an equimolar concentration of 11.8 g per liter.

Processing Composition G

Same as D, except that the ETA was Control ETA Compound D at an equimolar concentration of 10.2 g per liter.

CONTROL ETA COMPOUND C 4,4-dimethyl-1-p-tolyl-3-pyrazolidinone

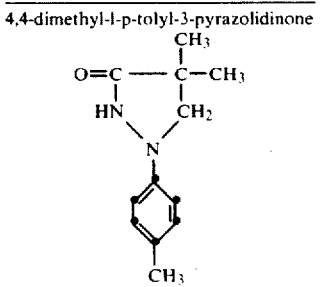

-continued
CONTROL ETA COMPOUND D
1-p-tolyl-3-pyrazolidinone

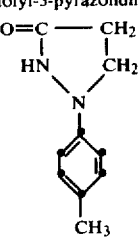

After processing, the elements were examined for physical deformities. These physical deformities took the form of bubbles or crystals. These can be counted by magnifying the picture area and counting the deformities in a representative square centimeter. Bubbles cause a physical degradation of the image and are quite objectionable. Crystals are objectionable if they are of a sufficient size to deform the film support. The following results were obtained:

TABLE

| Processing Composition | ETA | Bubbles/cm$^2$ $D_{max}$ Area of Print | Bubbles/cm$^2$ $D_{min}$ Area of Print | Crystals/cm$^2$ $D_{max}$ Area of Print | Crystals/cm$^2$ $D_{min}$ Area of Print |
|---|---|---|---|---|---|
| D | Compound 1 | 0 | 0 | 0 | 0 |
| E | Control ETA Compound B | 0 | 168 | 0 | 0 |
| F | Control ETA Compound C | 560 | 64 | 0 | 0 |
| G | Control ETA Compound D | 0 | 4 | 128 | 40 |

The above results indicate that the ETA according to the invention was the only one tested which did not give any objectionable crystals or bubbles, in comparison with closely-related compounds of the prior art.

EXAMPLE 7

Silver Development Rates for Various ETA's

An integral imaging receiving element was prepared which is similar to that of Example 5, except that the opaque layer 3 was omitted. Samples of this element were exposed and processed in the same manner as in Example 5 using the following processing composition:

| Processing Composition H | | |
|---|---|---|
| Potassium hydroxide (45 percent aqueous solution) | 104 | g |
| Sodium sulfite | 1.0 | g |
| 5-Methylbenzotriazole | 4 | g |
| Control ETA Compound B | 0.058 | M. |
| 1,4-Cyclohexanedimethanol | 3 | g |
| Sodium salt of naphthalene-formaldehyde condensate | 3 | g |
| | 6.4 | g |
| Potassium fluoride . 2H$_2$O | 10.0 | g |
| Carboxymethylcellulose | 44.0 | g |
| Water to 1 liter | | |

Processing Composition I

Same as H, except that the ETA was Control ETA Compound E.

Processing Composition J

Same as H, except that the ETA was Control ETA Compound F.

Processing Composition K

Same as H, except that the ETA was Control ETA Compound G.

Processing Composition L

Same as H, except that the ETA was Control ETA Compound H.

Processing Composition M

Same as H, except that the ETA was Control ETA Compound I.

Processing Composition N

Same as H, except that the ETA was Control ETA Compound J.

Processing Composition O

Same as H, except that the ETA was Compound 1.

Processing Composition P

Same as H, except that the ETA was Compound 2.

Processing Composition Q

Same as H, except that the ETA was Compound 6.

CONTROL ETA COMPOUND E

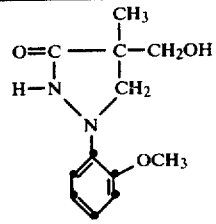

CONTROL ETA COMPOUND F

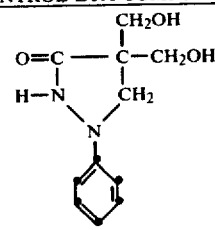

CONTROL ETA COMPOUND G

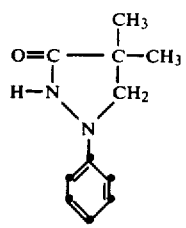

CONTROL ETA COMPOUND H

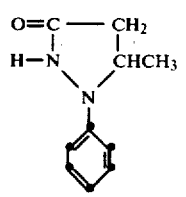

CONTROL ETA COMPOUND I

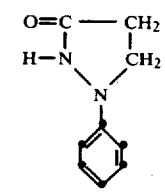

CONTROL ETA COMPOUND J

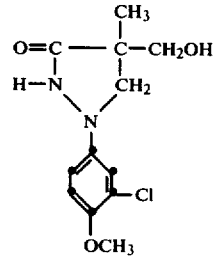

The infrared reflection densities of the samples were measured with a densitometer by scanning through the transparent support of the photographic element. From a plot of relative infrared density versus time of development, an accurate indication of silver development rates can be determined. The time required to reach one-half of the maximum density (t ½) was then determined for each ETA tested, amd was as follows:

| Processing Composition | ETA | t ½ (seconds) |
|---|---|---|
| H | Control ETA Compound B | 34 |
| I | Control ETA Compound E | 67 |
| J | Control ETA Compound F | 33 |
| K | Control ETA Compound G | 40 |
| L | Control ETA Compound H | 38 |
| M | Control ETA Compound I | 31 |
| N | Control ETA Compound J | 37 |
| O | Compound 1 | 21 |
| P | Compound 2 | 23 |
| Q | Compound 6 | 25 |

SILVER DEVELOPMENT RATES

The above data indicate that the ETA's of the invention have a faster silver development rate than those of closely-related prior art compounds.

The invention has been described in detail with particular reference to preferred embodiments thereof, but it will be apparent that variations and modifications can be effected within the spirit and scope of the invention.

What is claimed is:

1. In a dye image-receiving element comprising a support having thereon a dye image-receiving layer, the improvement wherein said element contains a silver halide electron transfer agent precursor having the following formula:

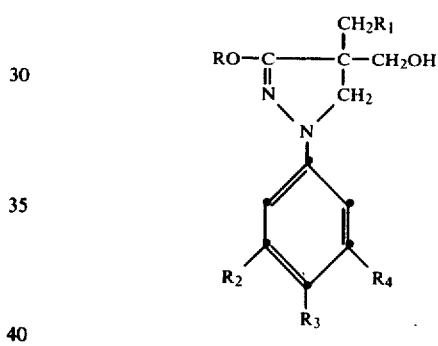

wherein:

R is hydrolyzable moiety;

$R_1$ is hydrogen or a hydroxy group;

$R_2$, $R_3$ and $R_4$ each represent hydrogen, hydroxy, an alkyl group of 1 to 3 carbon atoms, an alkoxy group of 1 to 3 carbon atoms, a phenyl group, —NHSO$_2$R$_5$, —O(CH$_2$)$_n$OR$_6$, —(CH$_2$)$_n$OR$_6$, —O(CH$_2$)$_n$C$_6$H$_5$, —(CH$_2$)$_n$R$_7$ or —O(CH$_2$)$_n$R$_7$;

$R_5$ is hydrogen or an alkyl group of 1 to 3 carbon atoms;

$R_6$ is hydrogen or a methyl group;

$R_7$ is NHSO$_2$R$_5$ or SO$_2$NHR$_5$; and n is a positive integer of 1 to 2;

with the proviso that at least one of said $R_2$, $R_3$ and $R_4$ must be one of said groups other than hydrogen.

2. The dye image-receiving element of claim 1 wherein $R_1$ is hydrogen, $R_2$ is hydrogen, $R_3$ is an alkyl group of 1 to 3 carbon atoms, and $R_4$ is hydrogen.

3. The dye image-receiving element of claim 2 wherein $R_3$ is a methyl group.

* * * * *